(12) United States Patent
Ramachandran Iyer et al.

(10) Patent No.: US 8,062,861 B2
(45) Date of Patent: Nov. 22, 2011

(54) TISSUE SAMPLE PREPROCESSING METHODS AND DEVICES

(75) Inventors: Eswar Prasad Ramachandran Iyer, Manassas, VA (US); Daniel N. Cox, Centreville, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 273 days.

(21) Appl. No.: 12/389,154

(22) Filed: Feb. 19, 2009

(65) Prior Publication Data

US 2009/0215112 A1     Aug. 27, 2009

Related U.S. Application Data

(60) Provisional application No. 61/030,452, filed on Feb. 21, 2008, provisional application No. 61/114,289, filed on Nov. 13, 2008.

(51) Int. Cl.
     *G01N 1/30*      (2006.01)
(52) U.S. Cl. .................................................. 435/40.52
(58) Field of Classification Search ........................ None
See application file for complete search history.

(56) References Cited

U.S. PATENT DOCUMENTS

| | | | |
|---|---|---|---|
| 3,879,106 A | | 4/1975 | McCormick |
| 4,695,339 A | * | 9/1987 | Rada ................................ 156/80 |
| 5,153,136 A | * | 10/1992 | Vandenburgh ............. 435/286.1 |
| 7,731,662 B2 | * | 6/2010 | Anderson et al. ............. 600/459 |

FOREIGN PATENT DOCUMENTS

EP     0884394 A2     12/1998

OTHER PUBLICATIONS

Stack et al. "Staining Plant Cell with Silver. The Salt-Nylon Technique." Biotechnic & Histochemistry, 1991: vol. 66, No. 2, pp. 69-78.*
Kodama et al. "An improved silver staining technique for nucleolus organizer regions by using nylon cloth." Journal of Human Genetics, Sep. 1, 1980, Springer, Japan. vol. 25, Issue 3, pp. 229-233.*
Stack, et al., Staining Plant Cells with Silver. I The Salt-Nylon Technique. Biotechnic & Histochemistry, 1991: vol. 66, No. 2 , pp. 69-78.
Kodama, et al., An improved silver staining technique for nucleolus organizer regions by using nylon cloth. Journal of Human Genetics, Sep. 1, 1980, Springer Japan, vol. 25, Issue 3, pp. 229-233.
International search report on patentability, PCT/US 2009/034608.

* cited by examiner

*Primary Examiner* — Ann Lam
(74) *Attorney, Agent, or Firm* — Brendan Baggot; David Yee

(57) ABSTRACT

To preprocess a tissue sample, a first permeable mesh membrane is tautly stretched out over the tissue sample and overlaid on top of a flat surface. This covering sandwiches and secures the tissue sample in between the first permeable mesh membrane and the flat surface. If it is desired to reinforce the mechanical strength of the first permeable mesh membrane, a second permeable mesh membrane can be tautly stretched out and overlaid on top of the sandwich. Alternatively, the second permeable mesh membrane can be attached onto a third component, such as a disposable solvent resistant frame, to create a framed mesh. Thereafter, the first permeable mesh membrane may be attached to the framed mesh to create a compound framed mesh. The tissue sample may then be sandwiched and secured in between the compound framed mesh and the flat surface. To retain and flatten the tissue sample, gentle pressure may be uniformly applied.

14 Claims, 5 Drawing Sheets

US 8,062,861 B2

TISSUE SAMPLE PREPROCESSING METHODS AND DEVICES

CROSS REFERENCE TO RELATED APPLICATIONS

The present application claims the benefit of provisional patent application Ser. No. 61/030,452 to Eswar Prasad Ramachandran Iyer et al., filed on Feb. 21, 2008, entitled "Methods and Device for Tissue Processing," and provisional patent application Ser. No. 61/114,289 to Eswar Prasad Ramachandran Iyer et al., filed on Nov. 13, 2008, also entitled "Methods and Devices for Tissue Processing," which are both hereby incorporated by reference.

BACKGROUND OF THE INVENTION

Many commonly used research methods, including cellular imaging via light and confocal microscopy, immunohistochemistry and fluorescent in situ hybridizations require the processing of thin and/or thick biological tissue sections over a glass slide or a glass-coverslip. If the tissue sections are well prepared and flat, and if the glass surface is clean, then the weak non-ionic forces, like hydrogen bonds and van der Waals forces, help the tissue sections to adhere to the glass surface.

However, often the tissue sections are not completely flat. Also, the slide surface may contain dust particles that can prevent good surface contact. Moreover, some tissue types do not even adhere to a slide or glass surface at all. Because of such problems, tissue sections are generally lost during tissue processing, which leads to wasted time and energy and rising costs.

For those sections that do adhere, tissue adhesion is generally not strong enough to withstand the mechanical stress of tissue processing. Examples of mechanical stress include, but are not limited to, long incubation periods in various chemicals, high temperatures and repeated washing in various solutions. Although these examples may be imperative to achieve successful processing of tissues, long processing times and repeated physical manipulation can dislodge the tissue.

The most commonly used method for preventing the dislodging of tissue sections is by coating the glass surface with various adhesives. Examples of adhesives include poly-L-Lysine (pLL), silane, glue (e.g., Elmer's glue), Mayere's egg albumin, chrome alum and chrome gelatin, silicon rubber, and starch paste. Another method involves creating a charged slide by using a known adhesive, such as pLL and silane.

There are a number of commercial products (e.g., adhesives and/or charged slides) that are available in the market that are aimed at improving the tissue retention. But, none of these completely solves the problem. Nonlimiting examples include Tissue-Tack Adhesive (Proscitech of Queensland, Australia), Biobond Tissue Section Adhesive (SPI Supplies of West Chester, Pa.), Superfrost Plus Gold Slides (Electron Microscopy Sciences of Hatfield, Pa.), Superfrost Plus Gold Slides (Erie Scientific Company of Portsmouth, N.H.), BD BioCoat Precoated Glass Coverslips (BD Biosciences of San Jose, Calif.), SUPERFROST PLUS—Adhesion (Electron Microscopy Sciences of Hatfield, Pa.), Poly-L-Lysine Coated and Silane Treated Microscope Slide (Electron Microscopy Sciences of Hatfield, Pa.), Excell Adhesion Slides (Electron Microscopy Sciences of Hatfield, Pa.), and Polysine Microscope Adhesion Slide (Electron Microscopy Sciences of Hatfield, Pa.).

It is even more challenging to mount thick tissue specimens. For example, a Drosophila cuticle has an uneven surface morphology and is more prone to curling up during dehydration. For some protocols, like immunohistochemistry, it is essential to dehydrate the cuticle well before mounting them for microscopy.

Conventionally, dehydration of the Drosophila larval cuticle is performed by mounting the filleted, fixed, and stained larval cuticle over a poly-L-Lysine (pLL) coated coverslip. Then, it is immersed sequentially into 30%, 50%, 90%, 100% and 100% ethanol solutions (~5 minutes each). Finally, the cuticle cleared twice in xylene to remove the ethanol and make the sections optically transparent (~10 minutes each).

Due to the thickness and uneven surface of the larval cuticle, it is very difficult to retain the tissues over the coverslip while maintaining section flatness during the dehydration process. A considerable percent of tissues usually dislodge from the glass surface due to insufficient adhesion to the coverslip. Once dislodged, it is difficult to recover the tissue for further analysis. Some tissues, even though not completely dislodged, curl in the edges, rendering them unfit for analysis. Further, the conventional method of dehydrating the cuticle requires considerable practice and lots of handling with care to minimize the tissue loss during processing. For example, someone with just a few months of experience in the protocol may lose about 50%-70% of total tissues processed due to poor tissue retention. Even a person with considerable experience may lose about 20%-30% tissues regularly. The percent of tissue retained during dehydration tends also to be strongly affected by the quality of pLL coating on the coverslips, which may suffer from batch-to-batch variations.

Furthermore, some methods require harsh treatment of sections (e.g., antigen retrieval), resulting in loss of tissue. Simply, these methods, along with the ones above, cannot guarantee complete tissue retention.

Consequently, what is needed is a device that allows all kinds of tissues to be retained over a flat surface (e.g., slide, coverslip, etc.) during the tissue processing for analysis. The device should also prevent the tissues from loosing its flat morphology. Furthermore, the device should be able to withstand the harsh conditions of tissue processing without affecting the quality of tissue processing.

BRIEF DESCRIPTION OF THE SEVERAL VIEWS OF THE DRAWINGS

The accompanying drawings, which are incorporated in and form a part of the specification, illustrate an embodiment of the present invention and, together with the description, serve to explain the principles of the invention.

DETAILED DESCRIPTION OF THE INVENTION

The present invention relates to devices, as well as methods for making such devices, for preprocessing tissue samples of all kinds (i.e., animal, human, plant, insects, etc.). These tissue sample preprocessing devices enable one to maximize tissue sample analyses after the tissue sample has been processed.

Preprocessing refers to the mounting of one or more tissue samples on a flat surface (e.g., a glass slide, plastic slide, or coverslip) coupled with the retention of flat, even tissue morphology on the flat surface as a critical parameter in preparing the tissue sample(s) for processing, and ultimately, microscopic visualization and analyses.

Processing refers those chemical treatments necessary to properly prepare tissue samples for analyses. In this case for example, processing may be referred to as (1) dehydration of tissue samples through a graded series of ethanol treatments coupled with xylene treatments to optically clear otherwise opaque tissues; (2) de-paraffinization of paraffin-embedded tissue sections; and (3) performing immunohistochemistry on a flat surface that is mounting thick and/or thin tissue sections.

Preprocessing Examples

Figure 1:
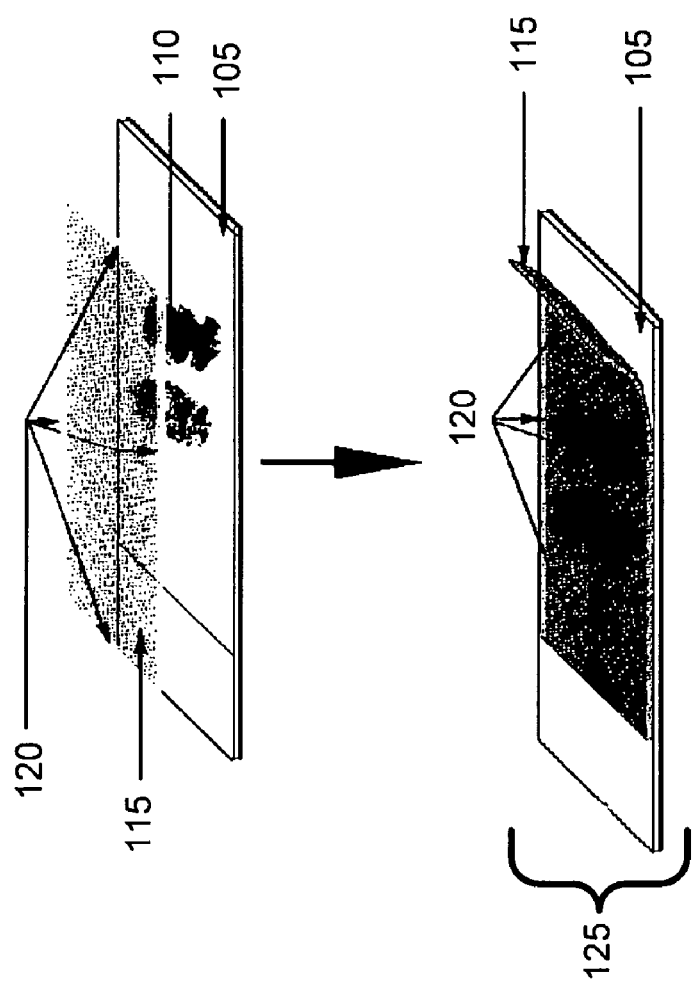
FIG. 1 shows an example of creating a tissue sample preprocessing/processing device.

Referring to FIG. 1 as one embodiment, a tissue sample 110 to be processed is placed on a flat surface 105. Once placed on the flat surface 105, a first permeable mesh membrane 115 is tautly stretched out over the tissue sample and overlaid on top of the flat surface. To secure the first permeable mesh membrane 115 on the flat surface 105, the edges of the first permeable mesh membrane 115 may be coated with a thin lining of solvent resistant adhesive 120 (e.g., adhesive film (peelable), acrylic adhesive, solvent resistant glue, etc.) to hold the first permeable mesh membrane 115 onto the flat surface 105. The effect is to securely sandwich the tissue sample between the first permeable mesh membrane and the flat surface, and thus creating a first permeable mesh membrane-tissue sample-flat surface sandwich 125.

The preprocessed tissue sample in this sandwich form is now ready to be processed using traditional, known methods (such as air drying; passing the samples through a chemical solution (e.g., methanol, ethanol, xylene, etc.) and/or a low surface tension solvent (e.g., Freon 113, hexamethyldisilazane); vacuuming; etc.). Additionally, tissue preprocessed in this manner is suitable for de-paraffinization of paraffin-embedded tissue sections and/or immunohistochemistry.

Because of the thickness of tissues tend to vary, the dimensions of the tissue sample preprocessing devices also tend to vary. As one embodiment, the resulting dimensions of the present invention may be ~75 mm long by ~22 mm wide by ~1 mm thick. As another embodiment, the dimensions may be ~75 mm long by ~22 mm wide by ~2 mm thick.

Flat surface 105 is defined to be any material that can be used for examining tissue samples. Examples include a slide (glass or clear plastic), coverslip, etc. Preferably, the flat surface 105 should be cleaned to remove dust, chemicals, oil, and any other foreign substance that may obstruct tissue processing.

The first permeable mesh membrane 115 is capable of being peeled away and discarded once tissue processing and/or analysis have been completed. To facilitate peeling, the first permeable mesh membrane 115 may include a flap on an edge.

To aid the flattening of the tissue sample 110, pressure may be uniformly and evenly applied on the first permeable mesh membrane-tissue sample-flat surface sandwich 125. The type of pressure includes pressing, compressing, thumbing, binder clipping, etc. The amount of pressure should be a uniform gentle force. Generally, this pressure may aid surface-to-surface contact between the tissue sample 110 and the flat surface 105. Furthermore, pressure may enhance tissue adhesion considerably.

The first permeable mesh membrane 115 also acts as a screen. At least two resulting effects emerge from screening the tissue sample. One, the screening acts as a protective barrier by rendering the tissue 110 resistant to repeated mechanical handling and washing. Two, the screening aids the removal of some uneven irregularities from any section of the tissue 110 without itself inducing any irregularities or scoring of the tissue sample surface.

Overall, this tissue screening feature surprisingly allows the processing of tissue sections in various solutions while minimizing the effects of stress handling on the tissues. Thus, greater tissue retention can be achieved.

Figure 2:
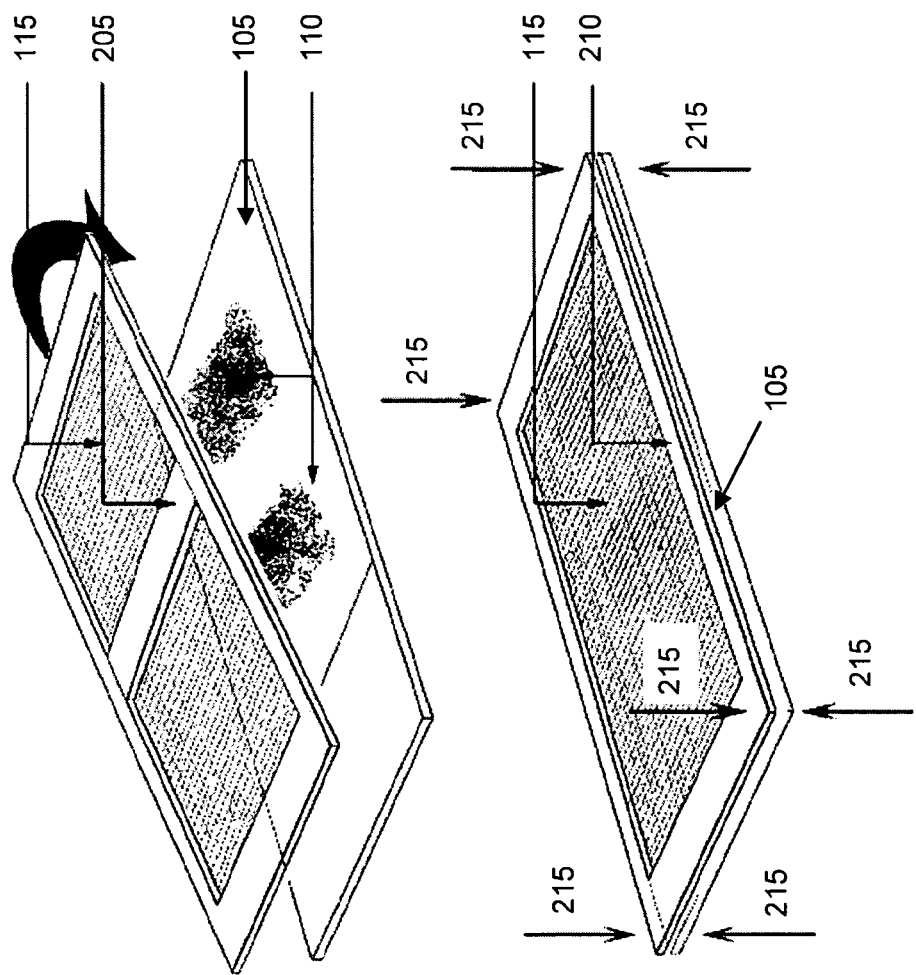
FIG. 2 shows another example of creating a tissue sample preprocessing/processing device.

Another embodiment is presented in FIG. 2. The first permeable mesh membrane 115 may be attached (via, for example, solvent resistant glue or adhesive, heat-melting, etc.) to a frame 205, such as a disposable plastic or glass frame. To allow multiple samples to be sandwiched on the flat surface 105 and be separated from each other simultaneously, the frame 205 may have two or more compartments. Each of these compartments are designed to confine a sample tissue for processing and/or analysis. For instance, the frame 205 may have a split-window for two coverslips (e.g., ~25 mm×~25 mm). Alternatively, the frame 210 may have a single large window. The former 205 may be used for smaller tissue samples 110; the latter 210 may be used for larger tissue samples 110. Solvent resistant adhesive 120 may be placed along the edges to secure the frame 205, 210 onto the flat surface 105. To further help set the frame in place and flatten the tissue sample(s), uniform pressure 215 may be applied on the frame.

Different kinds of mesh membranes with varying properties may be used according to the type of tissue selected for processing (i.e., dehydration, immunohistochemistry analysis, etc.). For instance, a mesh membrane may be hydrophilic or hydrophobic, or be neutral towards water affinity. Adsorption can be high, medium, low, or inert. The pH resistance can vary from ~1 to ~14. Some mesh may allow for high thermal stability (such as up to ~250° C.) to withstand some tissue processing protocols (such as antigen retrieval). Furthermore, each mesh can be sterilized in different ways as well, such as irradiation or be autoclavable.

Another important feature is that the mesh membranes should be highly resistant to chemical degradation. Furthermore, they should be heat resistant. Moreover, the mesh membranes should be strong and durable.

The mesh membranes may be made of varying types of material. Generally, they should be a fine, solvent-resistant, permeable membrane with a pore size sufficiently large to allow the free exchange of chemical and immunohistochemical reagents. Nonlimiting examples of meshes include nylon, stainless steel, polyester, polypropylene, fluorocarbon, polyetheretherketone, Fibralon, PTFE, polyethylene, etc. Each of the above described meshes is commercially obtainable from, for instance, Small Parts Inc. (Miramar, Fla.), which is a company specializing in materials for research and development.

Importantly, these meshes should also allow for the free mixing of solutions and reagents. To allow free mixing to occur, the pore size (i.e., pore opening diameter) of the meshes may vary from ~10 to ~100 microns. The percentage of open area of the mesh membranes may vary from ~1% to ~70%. In addition, the thread diameter of the mesh membranes may vary from ~10 to ~200 microns.

Figure 3:
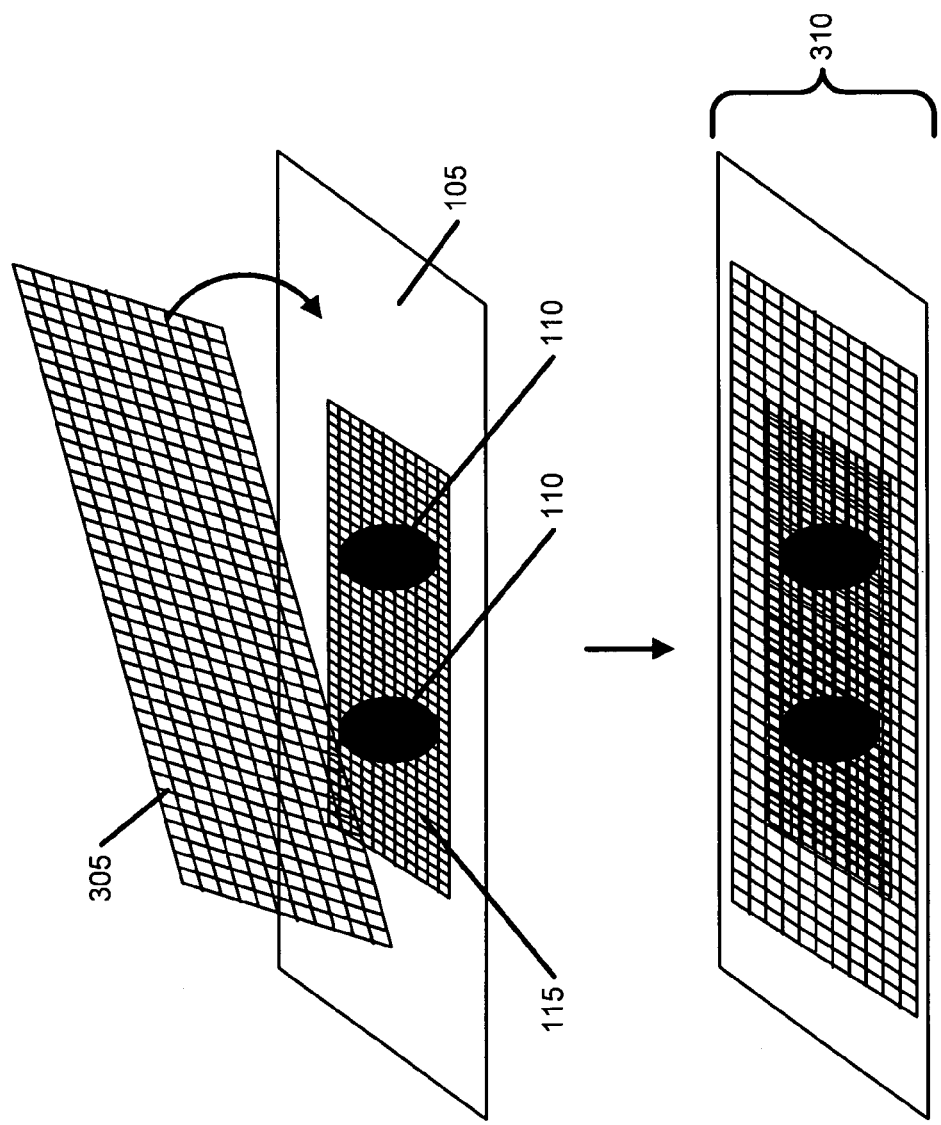
FIG. 3 shows another example of creating a tissue sample preprocessing/processing device.

Referring to FIG. 3, a second permeable mesh membrane 305 is introduced. In this example, the second permeable mesh membrane 305 acts mainly as a mechanical support for the first permeable mesh membrane 115. Building onto the above exemplified first permeable mesh membrane-tissue sample-flat surface sandwich 125, the second permeable mesh membrane 305 can be stretched and overlaid onto the first permeable mesh membrane-tissue sample-flat surface sandwich 125. In such case, the second permeable mesh membrane 305 may reinforce the durability of the first permeable mesh membrane 115 and simultaneously maintain the flatness of the tissue sample 110. To hold the second permeable mesh membrane 305 in place, solvent resistant adhesive 120 may be applied to the edges prior to mounting the second permeable mesh membrane 305 on top of the first permeable mesh membrane 115. Uniform gentle pressure 215 may then be applied to contact the second permeable mesh membrane 305 with the first permeable mesh membrane-tissue sample-flat surface sandwich 125. The result may be called a second permeable mesh membrane-first permeable mesh membrane-tissue sample-flat surface sandwich 310.

The second permeable mesh membrane 305, as well as any additional mesh membranes that may be used, can be of the same or equivalent types as the first permeable mesh membrane. Hence, as one embodiment where the device implements multiple mesh membranes, the first permeable mesh membrane is a fine Nitrex nylon mesh and the second permeable mesh membrane is a coarse nylon mesh. The sieve size of the fine Nitrex nylon mesh may vary from ~10 µm to ~100 µm. As one aspect, the first permeable mesh membrane has a sieve size of ~30 µm.

With respect to the coarse nylon mesh, it should have a relatively large sieve size. For instance, the selected sieve size may be ~300 µm. However, the sieve size may range anywhere from ~100 µm to ~500 µm. The open area may be ~50%. For a coarse nylon mesh having a size of ~30 cm×~30 cm, the thickness may be ~200 µm.

Figure 4:
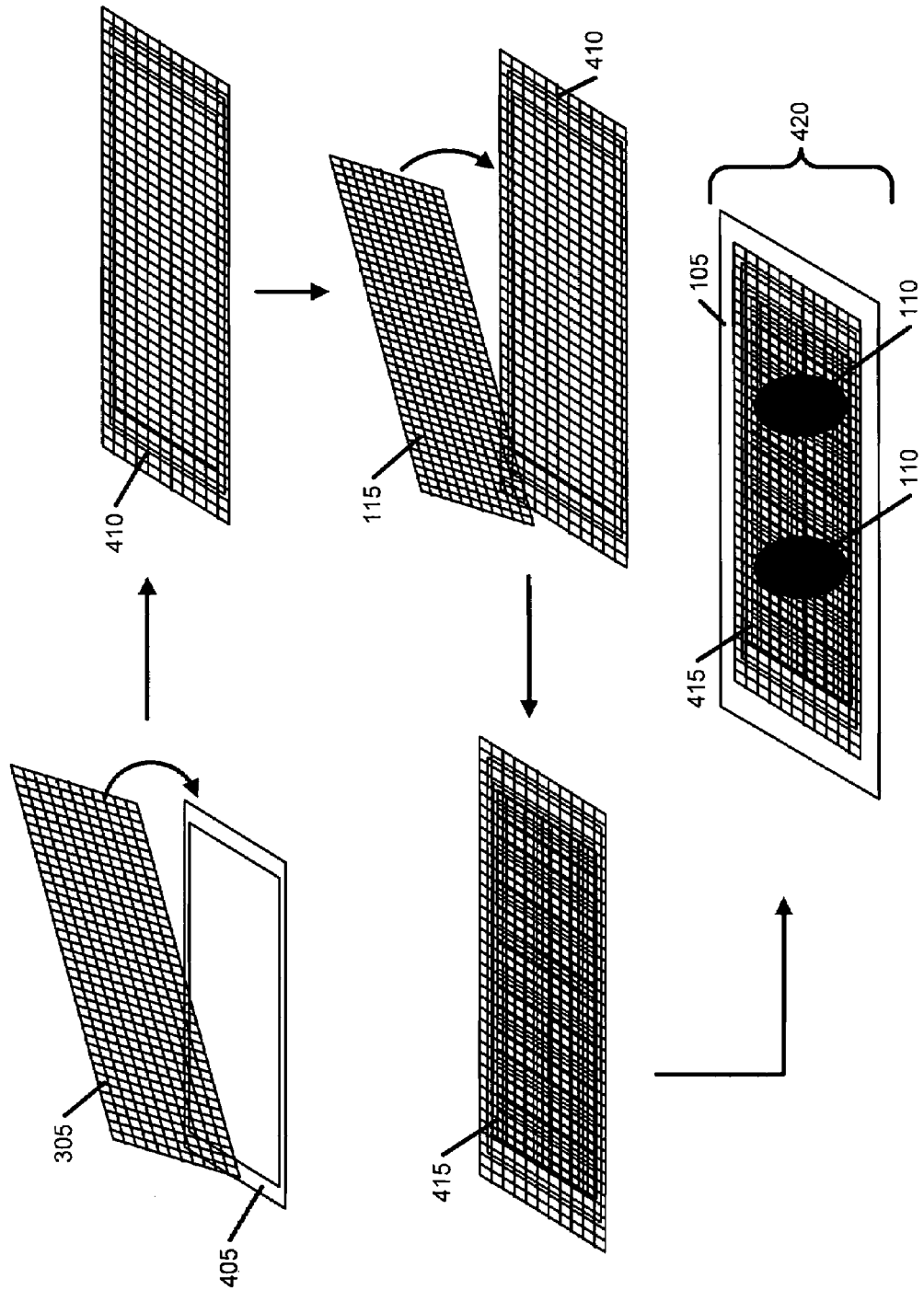
FIG. 4 shows another example of creating a tissue sample preprocessing/processing device.

In yet another embodiment, as shown in FIG. 4, a third component 405 may be integrated. Examples of the third component include a durable, solvent resistant metallic frame, durable solvent resistant plastic frame, a disposable slide unit with or without closeable flaps, etc. Where the third component 405 is a solvent resistant metallic frame, the dimensions of the metallic frame may be, for example, ~75 mm long×~25 mm wide×~1 mm thick, with an inner opening of ~40 mm long×~15 mm wide.

The second permeable mesh membrane 305 may be attached over third component 405 to create a framed mesh 410. To adhere the second permeable mesh membrane 305 to such metallic frame 405, a solvent resistant adhesive 120 (e.g., acrylic, cyanoacrylamide, solvent resistant glue, etc.) may be used. To further secure the adhered second permeable mesh membrane 305 onto the third component 405, the adhered second permeable mesh membrane 305 may also be heat-melted onto the third component 405. Thereafter, the first permeable mesh membrane 115 may be stretched, glued, and heat-melted over the second permeable mesh membrane 305 to create a compound framed mesh 415. This compound framed mesh 415 may then be used to sandwich the tissue sample onto a flat surface, creating a first permeable mesh membrane-second permeable mesh membrane-third component-tissue sample-flat surface sandwich 420.

Processing Examples

After mounting the tissue sample using any of these embodiments (preprocessing steps), the tissue sample may be processed by placing the assembly in a container of required dimensions (for example, a 50 ml conical tube) containing the appropriate solution and left undisturbed or over a gyrating nutator mixer or a shaker for a prescribed incubation time.

Then, after each incubation, if required, the excess solution may be drained from the assembly by tilting and touching one corner over an absorbent tissue. Independent of tissue type, once the protocol is complete, the membrane(s) and/or frame may be gently pulled apart, leaving the tissues intact over the flat surface. The flat surface with the tissues may then be removed and be subjected to further analysis (e.g., microscopic imaging, etc.).

For instance, for dehydration of *Drosophila* larval cuticle, an approximate incubation time of ~5 to ~10 minutes in each ethanol concentration and xylene solution is required. Incubation times may vary widely depending on the tissue type, reagents used, and the specific protocol implemented.

A second example involves the processing of human tissue samples, such as those from normal or diseased tissue that has been embedded for tissue sectioning (thick or thin) in paraffin. Human tissue samples include, but are not limited to, breast, lung, heart, colon, prostate, epidermis, blood vessels, stomach, intestines, kidney, eyes, brain, etc. Once paraffin-embedded tissue sections are mounted on a flat surface, these tissue sections can be processed using any of the above methods and devices. A nonlimiting example of processing includes an initial de-paraffinization of tissue section necessary for subsequent tissue processing procedures. This stage of tissue processing tends to be highly susceptible to tissue dislodgement from the mounting surface. Upon successful de-paraffinization, the tissue sections mounted on the device can then be processed for standard immunohistochemistry analyses and, where appropriate, for ultimate microscope visualization.

Advantages

Figure 5:
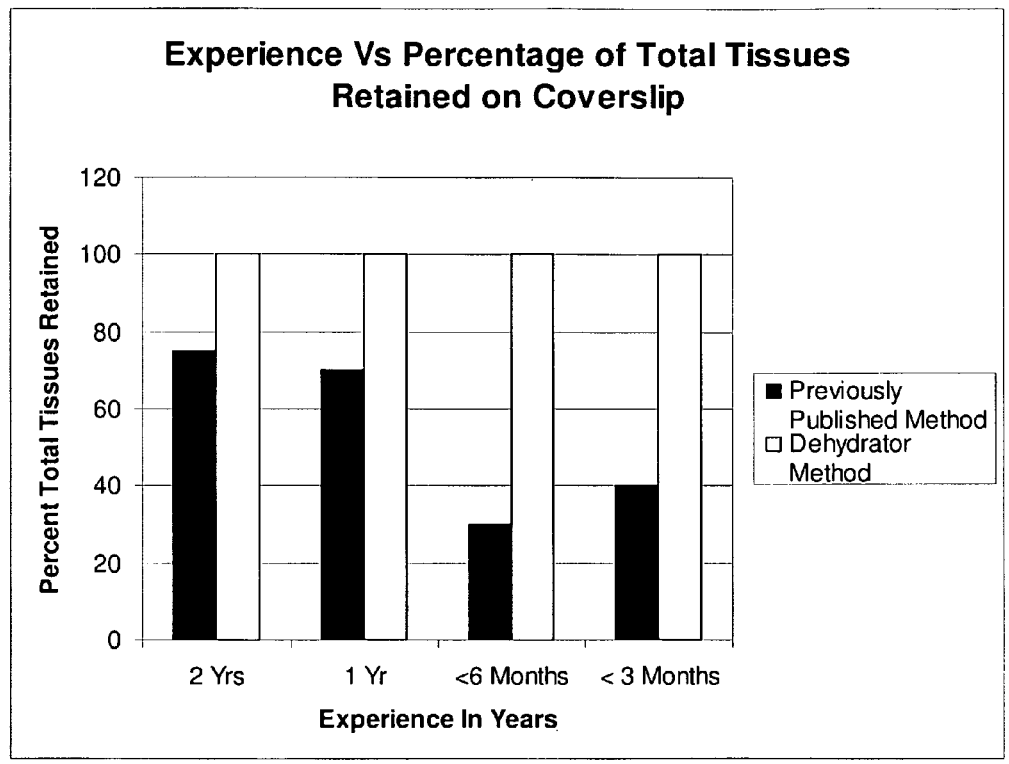
FIG. 5 shows a chart indicating the surprising results of tissue retention.

These methods of tissue retention offer numerous advantages over the conventional methods of tissue retention. First, as in the case of retaining tissue from *Drosophila*, as shown in FIG. 5, the improved methods generally offer nearly 100% tissue retention (such as during the dehydration step of a *Drosophila* larval cuticle for performing immunohistochemical analysis). These surprising results sharply contrasts results generally obtained through conventional methods of mounting *Drosophila* larval cuticle during immunohistochemistry, which often offer only ~70%-~75% tissue retention, even by an experienced user, and suffer from batch to batch variations in pLL coating of the slide or coverslip.

Second, little to no previous experience is required for mounting and processing tissue samples successfully. Even an inexperienced user can accomplish nearly 100% tissue retention during tissue processing by using this new method. But, under the conventional way, considerable amount of training and experience is required. Users with just a few months of experience may only be able to retain ~30% to ~40% of the tissues using the conventional method.

Third, the new way improves tissue quality by allowing mild agitation during processing to enhance fluid mixing, such as during the dehydration process of *Drosophila* larval cuticle prior to imaging analysis or in tissue de-parafinization and immunohistochemistry of human tissue samples. The conventional method creates poor mixing of fluids during dehydration.

Fourth, the new method is highly tolerant to mechanical handling during tissue processing. The conventional method offers very mild tolerance to mechanical handling due to poor adhesion to the slide or the coverslip.

Fifth, efficiency in the new method remains unaffected by batch-to-batch variation of pLL coating quality. On the contrary, efficiency in the conventional method is usually affected by batch-to-batch variation of pLL coating quality.

Sixth, the new method enables very flat tissue sections, with minimal deformation during dehydration. The tissue sections using the conventional method, however, are prone to mechanical deformation, such as curling and lipping edges.

In essence, the above described tissue processing device prevents tissue loss during the dehydration of tissue samples, such as a *Drosophila* larval cuticle, as well as in the processing of thick or thin paraffin-embedded tissue sections for immunohistochemistry. Such loss prevention save considerable amount of time, money, and precious reagents by increasing the efficiency of processing. The embodied devices are very user-friendly and do not require extensive training or any previous experience. The membrane composition, pore size, and the geometry of the device can be modified and optimized for other applications, which demand tissue retention over a flat surface for various types of tissue processing.

The foregoing descriptions of the embodiments of the claimed invention have been presented for purposes of illustration and description. They are not intended to be exhaustive or be limiting to the precise forms disclosed, and obviously many modifications and variations are possible in light of the above teaching. The illustrated embodiments were chosen and described in order to best explain the principles of the claimed invention and its practical application to thereby enable others skilled in the art to best utilize it in various embodiments and with various modifications as are suited to the particular use contemplated without departing from the spirit and scope of the claimed invention. In fact, after reading the above description, it will be apparent to one skilled in the relevant art(s) how to implement the claimed invention in alternative embodiments. Thus, the claimed invention should not be limited by any of the above described example embodiments. For example, the claimed invention may be practiced over other types of tissue and under different clinical conditions (such as processing of human or animal tissue samples).

In addition, it should be understood that any figures, graphs, tables, examples, etc., which highlight the functionality and advantages of the claimed invention, are presented for example purposes only. The architecture of the disclosed is sufficiently flexible and configurable, such that it may be utilized in ways other than that shown. For example, the steps listed in any flowchart may be reordered or only optionally used in some embodiments.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the claimed invention of the application. The Abstract is not intended to be limiting as to the scope of the claimed invention in any way.

Furthermore, it is the applicants' intent that only claims that include the express language "means for" or "step for" be interpreted under 35 U.S.C. §112, paragraph 6. Claims that do not expressly include the phrase "means for" or "step for" are not to be interpreted under 35 U.S.C. §112, paragraph 6.

A portion of the claimed invention of this patent document contains material which is subject to copyright protection. The copyright owner has no objection to the facsimile reproduction by anyone of the patent document or the patent invention, as it appears in the Patent and Trademark Office patent file or records, but otherwise reserves all copyright rights whatsoever.

What is claimed is:

1. A tissue sample preprocessing device comprising:
   a. a first permeable mesh membrane; and
   b. at least one flat surface; and
      wherein the first permeable mesh membrane
         i. is tautly stretched out over a tissue sample and overlaid on top of the flat surface, sandwiching and securing the tissue sample in between the first permeable mesh membrane and the flat surface; and
         ii. has a sieve size of approximately 10 μm to approximately 100 μm.

2. The device according to claim 1, wherein the pressure is applied to the first permeable mesh membrane to flatten the tissue sample.

3. The device according to claim 1, further including a second permeable mesh membrane being tautly stretched out and over the sandwiched tissue sample.

4. The device according to claim 3, wherein the second permeable mesh membrane is a coarse nylon mesh membrane.

5. The device according to claim 3, wherein the second permeable mesh membrane has a sieve size of approximately 300 μm.

6. The device according to claim 1, further including a framed mesh comprising a second permeable mesh membrane attached to a third component, the third component being a durable, solvent resistant frame.

7. The device according to claim 6, wherein the first permeable mesh membrane is attached to the framed mesh to create a compound framed mesh.

8. The device according to claim 7, wherein the tissue sample is tautly sandwiched and secured in between the first permeable mesh membrane of the compound framed mesh, and the flat surface.

9. A method for preparing tissue samples for processing comprising sandwiching and securing a tissue sample in between a first permeable mesh membrane having a sieve size of approximately 10 to approximately 100 μm and a flat surface, wherein the first permeable mesh membrane is tautly stretched over the tissue sample and over the flat surface.

10. The method according to claim 9, further including wrapping a second permeable mesh membrane around the sandwiched tissue sample.

11. The method according to claim 10, wherein the second permeable mesh membrane is a coarse nylon mesh with a sieve size of approximately 300 μm.

12. The method according to claim 9, further including attaching a second permeable mesh membrane to a third component to create a framed mesh, the third component being a durable, solvent resistant frame.

13. The method according to claim 12, wherein the first permeable mesh membrane is attached over the framed mesh, creating a compound framed mesh.

14. The method according to claim 13, wherein the tissue sample is tautly stretched and secured in between the first permeable mesh membrane of the compound framed mesh, and the flat surface.

* * * * *